United States Patent

Jose

Patent Number: 5,306,256
Date of Patent: Apr. 26, 1994

[54] MEDICAL TUBING MOUNT

[76] Inventor: Rick Jose, 224 Old Brattleboro Rd., Hinsdale, N.H. 03451

[21] Appl. No.: 107,565

[22] Filed: Aug. 18, 1993

[51] Int. Cl.$^5$ ............................................. A61M 5/32
[52] U.S. Cl. ............................ 604/180; 128/DIG. 26
[58] Field of Search ...................... 604/180, 174, 179; 128/DIG. 26

[56] References Cited

U.S. PATENT DOCUMENTS

| | | | |
|---|---|---|---|
| 3,677,250 | 7/1972 | Thomas | 604/180 |
| 3,702,612 | 11/1972 | Schlesinger | 604/180 |
| 3,834,380 | 9/1974 | Boyd | 604/180 |
| 4,484,914 | 11/1984 | Brown | 604/180 |
| 4,583,976 | 4/1986 | Ferguson | 604/174 |
| 4,737,143 | 4/1988 | Russell | 604/180 |

Primary Examiner—John G. Weiss
Attorney, Agent, or Firm—Terry M. Gernstein

[57] ABSTRACT

A tube restraint includes a low profile one piece tube mount such as disclosed in U.S. Pat. No. 5,131,854 mounted on a base unit. The base unit includes medical adhesive on one side and has one or more wing straps flexibly attached to the side edges thereof. The wing straps are longer than the base unit is wide, and include adhesive on a top surface. The wing straps are spaced and offset from the tube mount, and are folded over the base unit once a tube is attached to the tube mount. The wing straps fix the tube to the base unit and also extend over the base unit to contact the patient adjacent to the base unit whereby the wing straps both anchor the tube to the base unit and further anchor the base unit in place. Once the tubing procedure is completed, the tube mount can be removed from the patient and discarded.

4 Claims, 1 Drawing Sheet

५,३०६,२५६

MEDICAL TUBING MOUNT

TECHNICAL FIELD OF THE INVENTION

The present invention relates to the general art of mounting elements, and to the particular field of mounting elements used to attach medical equipment to a patient.

BACKGROUND OF THE INVENTION

Many modern medical procedures, such as catheritzation, intravenous therapy, tube feeding, nasal gasture feeding, canulas for oxygen therapy, and the like, use flexible tubing for the introduction and excretion of fluid into and out of a patient's body. Tubing used in such procedures is usually secured to the patient by means of adhesive tape.

While adhesive tape seems to work to secure tubing to a patient for short durations, many health care workers and patients alike experience problems with long term attachment to the patient using adhesive tape. For example, the tape may fall off after a period of use.

Therefore, the art has included several proposed solutions to the problem of inefficient securing of tubing to patients. While these proposed solutions have been somewhat effective, they still have problems. These devices are also often cumbersome to use and may not be comfortable for the patient.

These proposed solutions also are often expensive for at least two reasons. First, they may not be reusable. In fact, reusable products are being phased out because of the danger of cross contamination. Discarding such devices may make the devices expensive. Second, many of these devices are expensive to begin with. These expensive devices are made even more expensive if they are discarded after use. Any cumbersome device may be simply left on the shelf and tape used in its place. This makes such devices expensive since they are not used.

Therefore, there is a need for a tubing restraint that is disposable, dependable, inexpensive and easy to use.

OBJECTS OF THE INVENTION

It is a main object of the present invention to provide a device for temporarily mounting a medical device, such as a tube, to a patient.

It is another object of the present invention to provide a tubing restraint for temporarily mounting a medical tube to a patient that securely holds the medical tube in place.

It is another object of the present invention to provide a tubing restraint for temporarily mounting a medical device, such as a tube, to a patient that securely holds the medical equipment in place without damaging that medical equipment.

It is another object of the present invention to provide a tubing restraint for temporarily mounting a medical device, such as a tube, to a patient that securely holds the medical equipment in place without damaging that medical equipment yet which will permit easy application and removal of the equipment and which, itself, can be easily placed and removed.

It is another object of the present invention to provide a tubing restraint for temporarily mounting a medical device, such as a tube, to a patient that securely holds the medical equipment in place without damaging that medical equipment which is disposable.

It is another object of the present invention to provide a tubing restraint for temporarily mounting a medical device, such as a tube, to a patient that securely holds the medical equipment in place without damaging that medical equipment and which is inexpensive to manufacture, store and use.

SUMMARY OF THE INVENTION

These, and other, objects are achieved by a tubing restraint that has a Y-shaped tubing mount mounted on a base unit. The base unit includes a pad having adhesive on one side thereof for attaching the pad to a patient. The base unit further includes two wing straps flexibly attached to the side edges of the base unit. Each wing strap is longer than the width of the base unit and can be folded over the base unit and each includes adhesive on one surface. Medical tubing is held in the tubing mount, and the adhesive on the wing straps attaches the tubing to the base unit to securely hold that tubing in place.

The base unit includes a pad having two adhesive surfaces, one of which has medical adhesive thereon. A second pad is attached to the just-mentioned pad and the Y-shaped tubing mount extends through the second pad. The wing straps fold over the top pad to attach tubing to that top pad.

Tubing is snapped into the tubing mount, the adhesive on the wing straps is exposed, and the wing straps are folded over to fix the tubing to the base unit.

This device is used once and is discarded. It can be provided in several sizes and shapes as desired as may be required for various medical tubing and medical procedures. The tubing mount is sized to prevent permanently deforming the tubing or otherwise interfering with the fluid flow through the tubing. The tubing mount stabilizes the device and adds strength and longevity to the device. Tubing can be pre-attached to the device by a tubing manufacturer, with the device being slidably movable on the tubing to accommodate an individual situation.

The device is removed by simply cutting the wing straps to free the tubing, removing the tube from the tubing mount and pulling the device from the patient. The tubing is removed from the tubing mount based on the medical procedures appropriate to the particular tube.

BRIEF DESCRIPTION OF THE DRAWING FIGURES

DETAILED DESCRIPTION OF THE PREFERRED EMBODIMENT OF THE INVENTION

Figure 1:
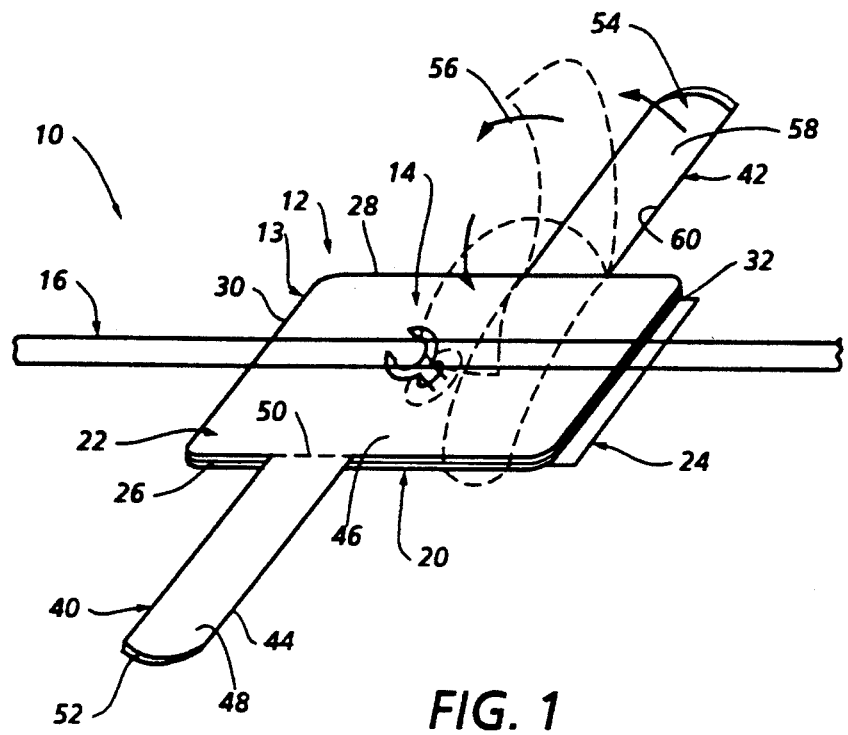
FIG. 1 is a top perspective view of the device embodying the present invention.
Figure 2:
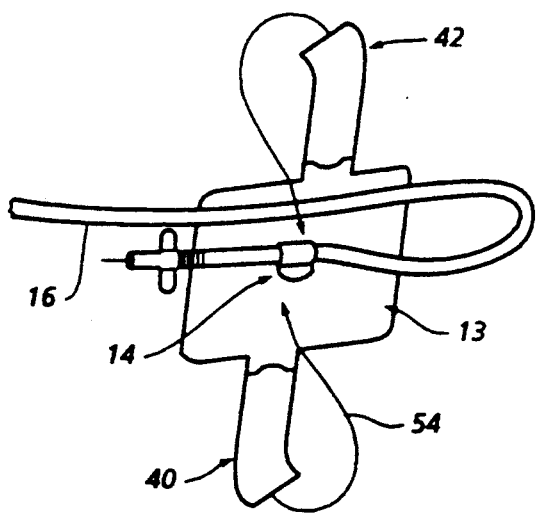
FIG. 2 is a top plan view of the device.

Shown in FIG. 1 is a tube mounting device 10 embodying the present invention. Device 10 includes a base unit 12 on which a tube mount 14 is mounted. Device 10 releasably mounts medical tubing 16 on a patient.

More specifically, base unit 12 includes a body 13 having a low density double faced adhesive coated polyethylene layer 20 having adhesive on one side for fixing the layer 20 to a top layer 22 formed of polyethylene foam. The other side of the layer 20 is covered with medical adhesive for attaching the device to a patient. A release cover 24 covers the medical adhesive and is removed to place device 10 on a patient. Base unit body 13 further includes two side edges 26 and 28 and two end edges 30 and 32, with a width dimension being defined between the two side edges 26 and 28 and a length dimension being defined between the two end edges 30 and 32. As shown in FIG. 1, the tubing extends lengthwise of the base unit, but could extend widthwise without departing from the scope of the present disclosure. Furthermore, while the base unit is shown as being rectangular, but can be any size, shape or dimension as required for a medical procedure.

The base unit further includes two wing straps 40 and 42 attached to the body 13. The wing straps are identical, and thus only wing strap 40 will be described. Wing strap 40 includes a body 44 having a top surface and a bottom surface, with the top surface being located adjacent to top surface 46 of the base unit, preferably co-planar therewith. Adhesive, such as medical adhesive, covers wing strap 40 on the top surface of that wing strap, and a release cover 48 covers the adhesive on the top surface of wing strap 40.

Wing strap 40 is flexibly attached to the body edge 26 at a proximal end 50 of the strap, and has a distal end 52 spaced from the body 13. The wing strap has a length dimension defined between the distal and proximal ends, with the wing strap length dimension being greater than the width dimension of the body 13 so the distal end of wing strap 40 extends away from the body edge 28 when the strap is in an overlapping position as shown for wing strap 42. The wing straps move in direction 54, and the release cover is removed as indicated by arrow 56 to expose adhesive 58 on top surface 60 of the wing strap.

As shown, both wing straps can be located on the same body side edge; however, the wing straps can be on opposite side edges if desired. In fact, any number of wing straps can be used, with two being shown for the sake of convenience. The wing straps are offset with respect to tube mount 14 so the wing straps can cover the tube as it enters and exits the tube mount. Preferably, the tube mount 14 is located centrally of the body, so the wing straps are offset with respect to that body center in one form of the invention.

Figure 3:
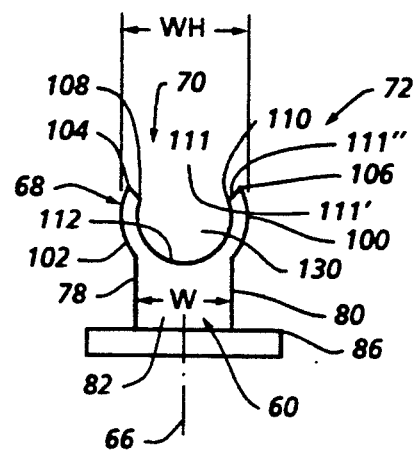
FIG. 3 is a front elevational view of a tubing mount used in conjunction with the device of the present invention.

The tube mount is identical to the electrical connector disclosed in U.S. Pat. No. 5,131,854, and the disclosure of this patent is incorporated herein by reference. However, for the sake of convenience, one figure of that patent is included herewith as FIG. 3. No detailed discussion of the mount are included here as such details are fully discussed in the referenced patent. It will only be noted that the tube mount includes a base 86 that is fixed to body 13 between layers 20 and 22 as also indicated in FIG. 1, a neck portion 80 connected to the base and extending upward therefrom to locate a C-shaped section 68 above top surface 46 of body 13. The C-shaped section includes two ends 70 and 72 that are sized, configured and spaced apart so that a tube can be received in the C-shaped section without permanently deforming the tube whereby normal fluid flow through the tube can be expected even when it is mounted on the device 10. The tube mount is preferably centrally located on the body 13. The tube mount can be plastic material, but can also be any other material suitable for medical applications. The tube mount also has a sloping entrance slot to facilitate entry of the tube into the tube mount, but to resist any tendency of the tube to slip our of the tube mount once it has been placed in that tube mount. As shown in FIG. 1, the wing straps are spaced from the center of the edges to which each is attached whereby the wing straps are spaced from the tube mount. In this manner, a tube being supported by the tube mount will be supported by the wing straps on either side of the tube mount, or at least one side of that tube mount.

As can be understood from the foregoing, the device is used by first locating it with respect to the patient near or at the position desired and then attaching tube 16 to tube mount 14 either by slipping that tube through the tube mount C-shaped section or by snapping that tube down into the C-shaped section between ends 70 and 72. Once the tube is fixed to the tube mount, the device can be moved to place it on the patient in the precise position desired by sliding the device along the tube. Once the device is in the precisely desired location and position, release cover 24 is removed, and the device 10 is adhered to the patient. Release covers 48 are removed from the wing straps, and those wing straps are folded over the tube and the body 13. The straps are then fixed to the tube, the body and to the patient's body (as the wing straps are longer than the body is wide). The straps thus serve a dual purpose of anchoring the tube and further anchoring the device 10 to the patient. Of course, variations in this method of attaching the device to a patient can be made depending on the situation as will occur to those skilled in the art based on the teaching of this disclosure.

The device is removed by simply cutting the wing straps on either side of the tube and removing the tube from tube mount 14 by either popping the tube out of the tube mount, or sliding the tube mount off of the tube. Once the tube is properly removed, the device 10 is removed by pulling it off of the patient in the manner of adhesive tape or other such medical device. The removed device is then discarded.

It is understood that while certain forms of the present invention have been illustrated and described herein, it is not to be limited to the specific forms or arrangements of parts described and shown.

I claim:

1. A means for temporarily mounting a medical tube to a patient comprising:
   A) a base unit which includes
      a body having a top surface, a bottom surface, side edges and a width dimension defined between said side edges,
      medical adhesive on said bottom surface,
      a release sheet covering said medical adhesive,
      wing straps on said side edges, each wing strap being flexibly attached to one of said side edges at a proximal end of said each wing strap and having a distal end spaced from said proximal end, each wing strap further including
      (a) a top surface which is adjacent to the top surface of said body and a bottom surface,
      (b) adhesive on the top surface of said each wing strap,
      (c) a release cover on the adhesive on said each wing strap,
      (d) each wing strap being sized to have a length dimension defined between said distal end and said proximal end which is greater than said width dimension; and
   B) a tube mount mounted on said base unit, said tube mount including a base fixed to said body,
a neck portion connected to said base,
a C-shaped portion connected to said neck portion, said tube mount being located between said side edges and being offset from said wing straps.

2. The means defined in claim 1 wherein said wing straps are offset from each other.

3. The means defined in claim 1 wherein said body includes a top layer and a low density double faced adhesive coated layer fixed to said top layer at one of the adhesive coated layers, said medical adhesive forming the other adhesive coated layer of said double face adhesive coated layers.

4. The means defined in claim 3 wherein said top layer includes polyethylene foam.

* * * * *